United States Patent [19]
Hagerty

[11] Patent Number: 5,709,652
[45] Date of Patent: Jan. 20, 1998

[54] TAMPON APPLICATOR TUBE HAVING APERTURED FINGER GRIP

[75] Inventor: Andrew J. Hagerty, Plainsboro, N.J.

[73] Assignee: McNeil-PPC, Inc., Skillman, N.J.

[21] Appl. No.: 496,103

[22] Filed: Jun. 28, 1995

[51] Int. Cl.$^6$ .................. A61F 13/20; A61M 31/00
[52] U.S. Cl. .................. 604/15; 604/18; 604/285; 604/288
[58] Field of Search .................. 604/11–18, 285, 604/286, 288, 904

[56] References Cited

U.S. PATENT DOCUMENTS

| | | | |
|---|---|---|---|
| 2,489,502 | 11/1949 | Ruth | 604/18 |
| 3,196,873 | 7/1965 | Bletzinger et al. | 604/15 |
| 3,534,737 | 10/1970 | Jones, Sr. | 604/18 |
| 3,884,233 | 5/1975 | Summey | 604/15 |
| 4,351,338 | 9/1982 | Langlois et al. | 604/904 |
| 4,412,833 | 11/1983 | Wiegner et al. | 604/14 |
| 4,508,531 | 4/1985 | Whitehead | 604/14 |
| 4,536,178 | 8/1985 | Lichstein et al. | 604/15 |
| 4,573,963 | 3/1986 | Sheldon | 604/15 |
| 4,573,964 | 3/1986 | Huffman | 604/15 |
| 4,755,164 | 7/1988 | Hinzmann | 493/288 |
| 4,891,042 | 1/1990 | Melvin et al. | 604/16 |
| 4,973,302 | 11/1990 | Armour et al. | 604/15 |
| 5,087,239 | 2/1992 | Beastall et al. | 604/14 |
| 5,267,953 | 12/1993 | Paul et al. | 604/15 |
| 5,279,541 | 1/1994 | Frayman et al. | 604/15 |
| 5,346,468 | 9/1994 | Campion et al. | 604/13 |
| 5,395,308 | 3/1995 | Fox et al. | 604/15 |
| 5,542,914 | 8/1996 | Van Iten | 604/11 |

FOREIGN PATENT DOCUMENTS 2148124  5/1985  United Kingdom ............ 604/15

Primary Examiner—Robert A. Clarke
Assistant Examiner—Dennis Ruhl

[57] ABSTRACT

The present invention relates to an insertion device formed of a tubular element capable of substantially containing an insertable element. The tubular element has an insertion end and a gripper end. The gripper end has a plurality of finger-accepting apertures. These apertures are dimensioned to accept a portion of a user's finger. This device is particularly useful in a tampon applicator tube which has a high-gloss outer surface.

39 Claims, 4 Drawing Sheets

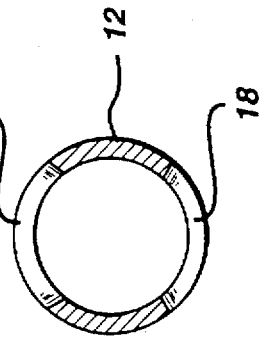
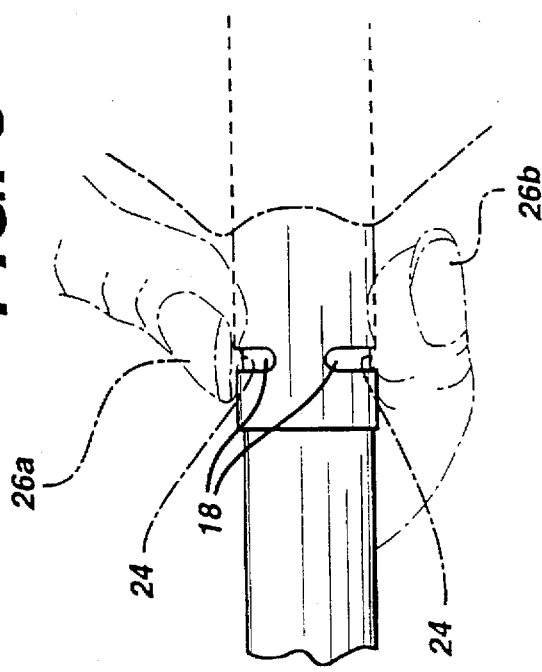
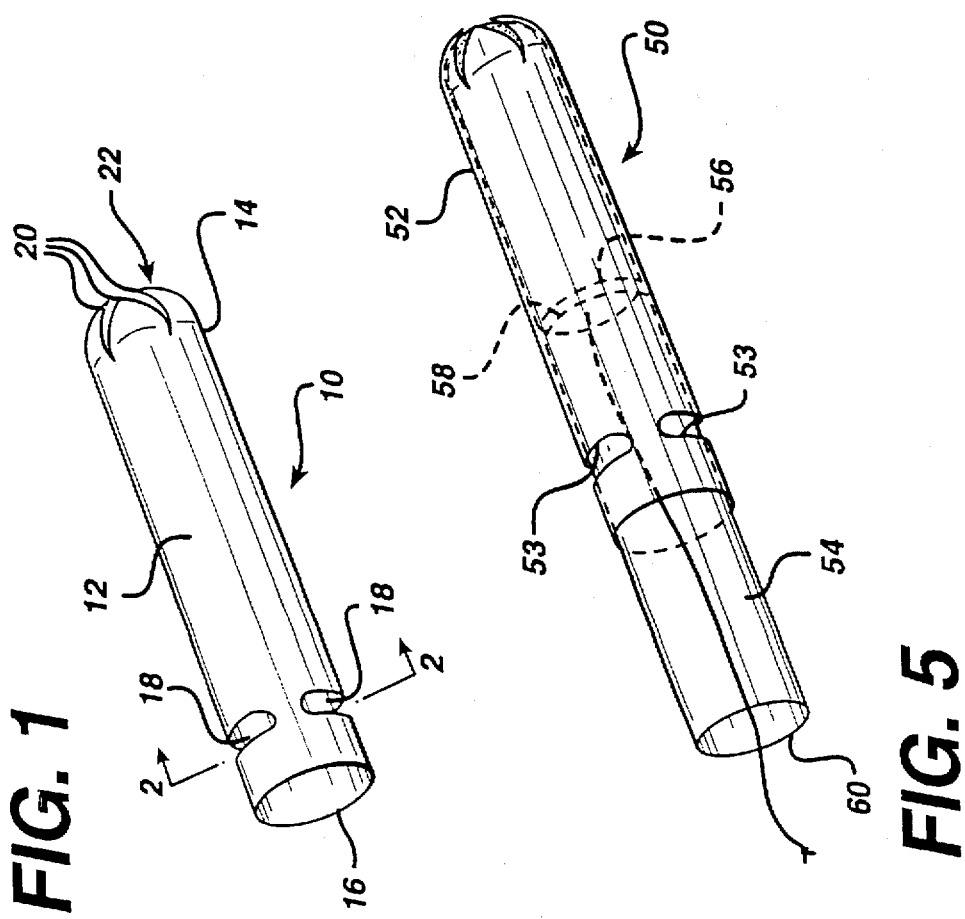

TAMPON APPLICATOR TUBE HAVING APERTURED FINGER GRIP

FIELD OF THE INVENTION

The present invention relates to tubular insertion devices having an apertured finger grip to improve the ability of a user to maintain a secure grip on the applicator tube during use. In particular, the insertion devices have a plurality of finger-accepting apertures in the gripper end of the tube.

BACKGROUND OF THE INVENTION

Tubular insertion devices, such as tampon applicators, are generally constructed of one of two basic materials: plastic and cardboard. These devices, whether cardboard or plastic, generally incorporate surface features at the rear or gripper end to allow the user to more or less securely hold the applicator during the following activities: inserting the device, ejecting a substantially enclosed element from the device, and withdrawing the device. Attempts have been made to add surface treatments to the gripper end of tampon applicator tubes in both plastic and cardboard devices. For example, Wiegner et al., U.S. Pat. No. 4,412,833, teaches a lightly grooved grip; Beastall et al., U.S. Pat. No. 5,087,239, teaches a series of more pronounced grooves forming rings in the gripper end; Hinzmann, U.S. Pat. No. 4,755,164, discloses both a grip area having a reduced diameter and surface indentations; and Whitehead, U.S. Pat. No. 4,508,531, and Huffman, U.S. Pat. No. 4,573,964, both teach finger grip areas having substantially reduced diameter. The finger grips disclosed in this prior art generally have a limited ability to prevent finger slip during insertion of the applicator and ejection of the tampon. In those finger grips which have some improvement in their ability to prevent finger slip, the production requires severe manipulation of applicator material to provide sufficient finger grip height.

Sheldon, U.S. Pat. No. 4,573,963, teaches a finger gripping section formed by a series of spaced, circumferentially disposed slits in conjunction with inwardly turned ribs. The inwardly projecting ribs reduce the effective inside diameter of the outer tube. Thus, the plunger used in conjunction with this outer tube must have a diameter which is substantially less than the outer tube.

In addition, tampon applicators on the market are moving toward the use of higher gloss surfaces which are more slippery than previously used cardboard applicator tubes. Therefore, attempts have been made to provide even more pronounced finger grip protrusions. For example, Campion et al., U.S. Pat. No. 5,346,468, discloses a cardboard tampon applicator having a polymeric coating on the outer tube and finger grip rings which have a height of at least 0.010 inches. This applicator requires even more violent manipulation of the applicator tube material.

In view of the shortcomings of the prior art, what is needed is a tampon applicator which has substantial resistance to finger slip while inserting the device, ejecting a substantially enclosed element from the device, and withdrawing the device without requiring severe manipulation of the device material during manufacture which may result in damage to this material or which may not provide sufficient protrusion to prevent finger slip.

SUMMARY OF THE INVENTION

The present invention relates to an insertion device formed of a tubular element capable of substantially containing an insertable element. The tubular element has an insertion end and a gripper end. The gripper end has a plurality of finger-accepting apertures in the surface thereof. These apertures are dimensioned to accept a portion of a user's finger. For example, they may be arranged and configured to allow the skin of a user's finger to project into the apertures. This insertion device is particularly useful in a device which has a high-gloss outer surface.

The insertion devices of the present invention may be used as tampon applicators for feminine hygiene. Another configuration of the insertion device may be for the vaginal or rectal delivery of prophylactic compositions and/or medicaments.

The invention also relates to a method of forming an insertion device. Thus, a tubular element capable of substantially containing an insertable element and having an insertion end and a gripper end is formed. A plurality of finger-accepting apertures are formed in the gripper end. The finger-accepting apertures are dimensioned to accept a portion of a user's finger. The finger-accepting apertures may be formed before or after tube-forming material is manipulated into the tubular element.

As used in the specification and claims, the term "aperture" and variants thereof, mean an opening in the surface of the tubular insertion device which forms a discontinuity in the tube-forming material at the edges of the opening, at least at the leading and trailing edges thereof. This aperture thereby provides relatively abrupt, finger-accepting edges to frictionally resist movement of a user's finger in response to longitudinal forces on the device.

BRIEF DESCRIPTION OF THE DRAWING

FIG. 1 is a perspective view of a tampon applicator tube according to the present invention.

FIG. 2 is a cross-section along line 2—2 of FIG. 1.

FIG. 3 is a side elevation of the gripper end of the tampon applicator tube of FIG. 1 during use.

FIG. 5 is a perspective view of a tampon applicator incorporating the tampon applicator tube of FIG. 1.

DETAILED DESCRIPTION OF THE INVENTION

Figure 4A:
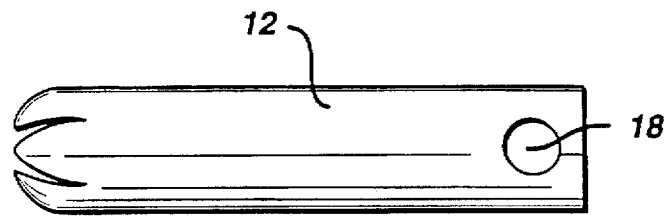
FIGS. 4A–4G are side elevations of tampon applicator tubes illustrating various finger-accepting apertures contemplated by the present invention.
Figure 4B:
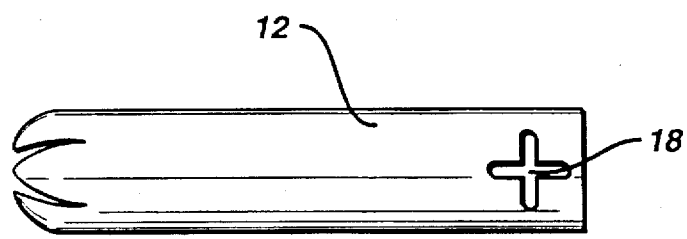
Figure 4C:
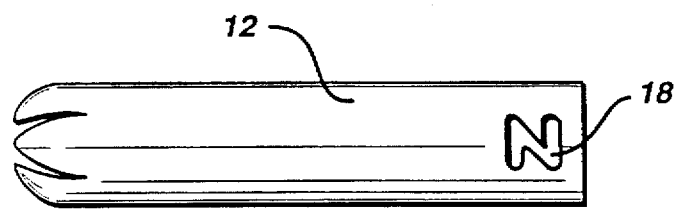
Figure 4D:
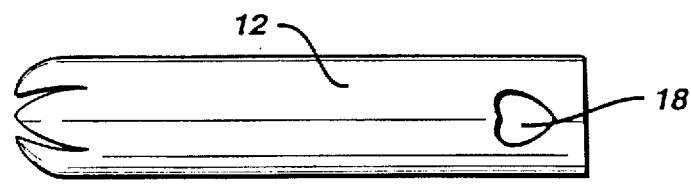
Figure 4E:
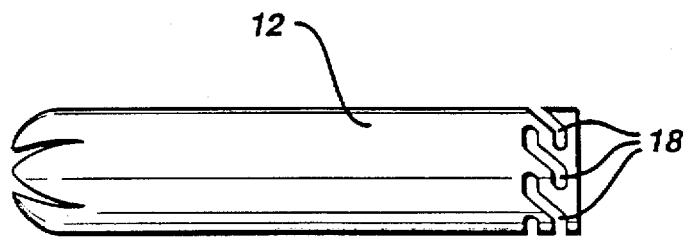
Figure 4F:
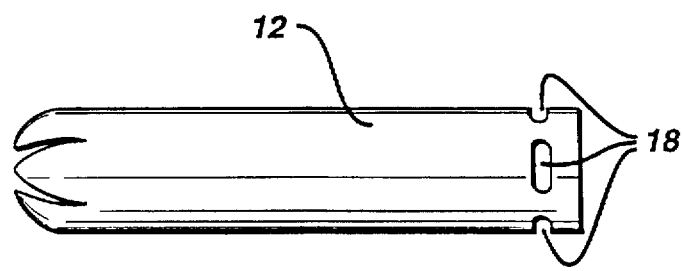

Referring to FIGS. 1–3, one embodiment of the present invention relates to a tampon applicator tube 10 formed of a tubular element 12 having an insertion end 14 and a gripper end 16. The gripper end 16 has a plurality of finger-accepting apertures 18. The insertion end 14 may have a plurality of inwardly curved petals 20 forming a substantially closed dome 22.

The finger-accepting apertures 18 of the gripper end 16 are dimensioned to accept a portion 24 of a user's finger 26. Experimentation has shown that a useful longitudinal dimension of the apertures 18 can vary from 1 mm or less to greater than 10 mm. Useful circumferential dimensions of the apertures 18 can vary from about 1 mm to greater than 20 mm. Preferably, the longitudinal dimension is about 1 mm to about 10 mm, and more preferably, about 6 mm to about 8 mm. Preferably, the circumferential dimension is about 3 mm to about 20 mm, and most preferably about 8 mm to about 16 mm. If the aperture dimensions are too large, the tube may lose stability necessary for processing and handling and the user's finger may project too far into the tube and clamp on a telescopically-enclosed plunger. If the aperture dimensions are too small, the user's finger will not sufficiently penetrate into the aperture to enhance the user's grip.

Figure 4G:
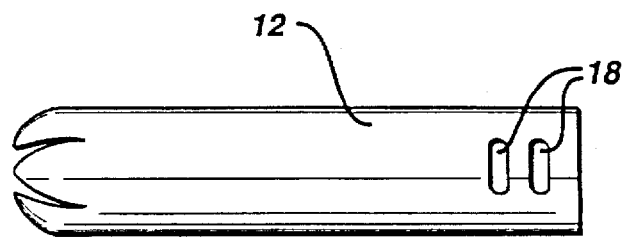

The finger-accepting apertures 18 are preferentially arranged circumferentially about the gripper end 16. These apertures 18 can be arranged in a single circumferential arrangement as illustrated in FIGS. 1, 3, 4A–4F, or they can be arranged in multiple circumferential arrangements as illustrated in FIG. 4G. The apertures 18 may be spaced apart in the circumferential direction by about 3 mm to about 20 mm, preferably about 4 mm to about 16 mm. Adjacent circumferential arrangements can be spaced apart in the longitudinal direction by about 3 mm to about 15 mm, preferably about 3 mm to about 6 mm.

The apertures 18 may take essentially any desired shape including circles, ovals, hearts, lines, alpha-numeric symbols, and various other geometric patterns. Representative, non-limiting examples of some of these apertures are illustrated in FIG. 4A–4G. Preferred apertures have at least one major axis which is in the circumferential direction. The apertures 18 may be arranged to provide a plurality of apertures 18 in each circumferential arrangement, preferably two to four apertures per circumferential arrangement, and more preferably, two apertures approximately oppositely disposed about the circumference. This more preferred arrangement allows a user to grip the applicator tube 10, usually between a finger 26a and a thumb 26b, on opposite portions of the gripper end 16.

A tampon applicator 50 is illustrated in FIG. 5. This applicator 50 includes an outer tubular element 52 having a pair of finger-accepting apertures 53 and an inner tubular element 54. While the outer tubular element 52 of FIG. 5 is similar to that described above in reference to FIGS. 1–3, it may also be configured like those tubular elements illustrated in FIGS. 4A–4G. The inner tubular element 54, or plunger, is used to expel a tampon 56 from the outer tubular element 52. Thus, the leading end 58 of the plunger 54 bears against the tampon 56 when a user's finger pushes the trailing end 60 of the plunger 54.

Figure 6:
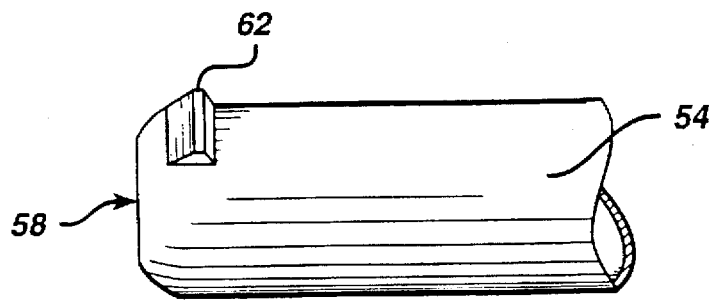
FIG. 6 is a side elevation of a plunger tube which can be used in the present invention.

Referring now to FIG. 6, the plunger 54 has at least one protrusion 62 proximate the leading end 58 which is engageable with at least one of the finger-accepting apertures 53. This protrusion 62 may also be dimensioned to be engageable with one or more of the embossed or indented grip-enhancing features described below.

The tampon applicator tubes of the present invention can be made of materials generally known to those of ordinary skill in the art. The applicators may be conventional plastic, such as injection-moldable or blow-moldable plastic, biodegradable plastic, such as those disclosed in the commonly assigned application, Dabi et al., U.S. Ser. No. 08/006,013, filed Jan. 15, 1993 (herein incorporated by reference), or cardboard. The cardboard used in tampon applicators can be a single layer of cardboard material, or it can be a plurality of laminated layers to provide multiple benefits relating to the various layers. Useful cardboard stock for the formation of the tubular elements include, without limitation, paperboard, cardboard, cup stock, paper, and the like. The laminated cardboard material may include a surface layer or coating of plastic, wax, silicone, and the like, which may be useful to increase the comfort to the user during insertion and withdrawal. The plastic coating may include, without limitation, polyolefins such as polyethylene and polypropylene, polyesters such as polyethylene terephthalate, polycaprolactone, polyvinyl alcohol, ethylene-vinyl acetate copolymers, cellophane, and the like.

Preferred tubular element materials include laminated cardboards. Preferred laminated cardboards include plastic laminated or plastic coated cardboard materials. These plastic laminated cardboard materials may include additional layers such as adhesive layers, tie layers, and the like.

Typical dimensions for the tubular elements useful in tampon applicators include a length of about 5 to 8 cm, a diameter of about 8 to 16 mm, and thicknesses of about 0.4 to 0.6 mm. Preferably, the diameter of the inner tubular element is less than the diameter of the outer tubular element to allow for a telescopic arrangement of the inner tubular element within the outer tubular element as shown in FIG. 5.

While it is believed that the use of finger-accepting apertures at the gripper end provides sufficient resistance to finger slip while inserting the applicator, ejecting the tampon from the applicator, and withdrawing the applicator, on occasion, it may be desirable to add additional grip-enhancing features to the gripper end of the outer tubular element in a tampon applicator. Possible grip-enhancing features include, without limitation, embossed or indented surfaces, protrusions, and the like. Preferably, these additional grip-enhancing features are used in close proximity to the finger-accepting apertures to provide more effective resistance to finger slip and to guide a user to correct finger placement.

Figure 7:
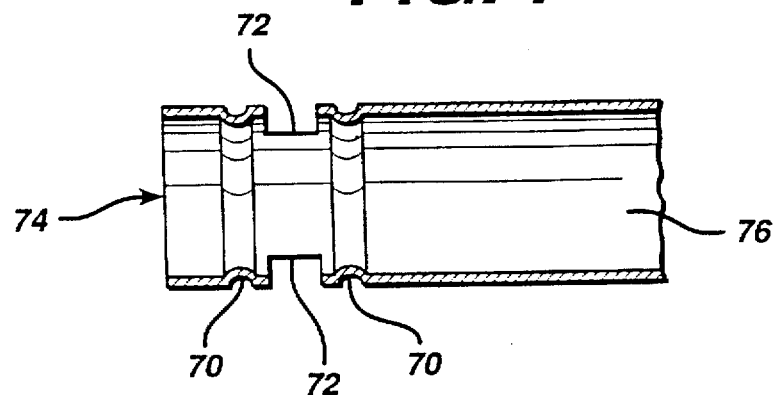
FIG. 7 is a cross-section of the gripper end of an alternative embodiment of the present invention incorporating indented surfaces adjacent a pair of finger-accepting apertures.

Embossed or indented surfaces may take the form of dots, grooves, and the like. An example of the use of an embossed surface in conjunction with finger-accepting apertures is illustrated in FIG. 7. In this embodiment, embossed surfaces 70 are positioned proximate a finger-accepting aperture 72 at the gripper end 74 of an outer tubular element 76 of a tampon applicator.

Figure 8:
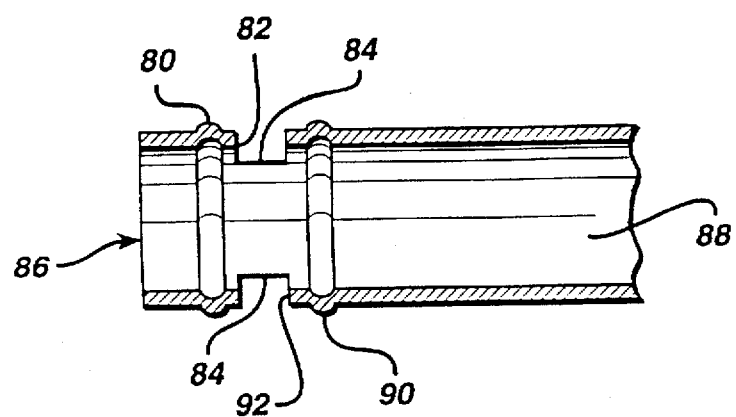
FIG. 8 is a cross-section of the gripper end of an alternative embodiment of the present invention incorporating projections adjacent a pair of finger-accepting apertures.

Protruding features may take the form of bumps, pyramids, rings, and the like. An example of the use of a protruding ring in conjunction with finger-accepting apertures is illustrated in FIG. 8. In this embodiment, a first raised ring 80 is positioned adjacent a rear edge 82 of a finger-accepting aperture 84 at the gripper end 86 of an outer tubular element 88 of a tampon applicator, and a second raised ring 90 is positioned adjacent a front edge 92 of the aperture 84.

The tubular elements of the present invention can be made from plastic or cardboard materials. When plastic is used in the practice of this invention, the tubular elements can be formed by injection molding, blow molding, rolled sheets, and the like. The finger-accepting apertures of the gripper end can be formed by means recognized by those of ordinary skill in the art. For example, the finger-accepting apertures can be formed during the molding of the tubular element, or they can be formed after the tubular element has been formed ("post-formed"). If the finger-accepting apertures are post-formed, the apertures may be obtained by die cutting, laser cutting, water jet cutting, thermoforming, grinding, and the like. The additional grip-enhancing features can also be formed during the molding of the plastic tubular elements or can be post-formed. Plastic tubular elements formed of rolled sheets can be formed as discussed below for cardboard stock.

Cardboard tubular elements can be formed in several ways currently known to those of ordinary skill in the art. The cardboard tubes may be formed as a continuous spiral-wound tube and subsequent cutting to form the tubular elements. On the other hand, rectangular sheets of cardboard can be rolled up to make individual tubular elements or shorter tubes having longitudinal seams. The shorter tubes can be cut to form a small number of tubular elements, similar to the continuous, spiral-wound tubes. When a continuous tube is used, the finger-accepting apertures and other optional grip-enhancing features will generally be post-formed. When shorter tubes having longitudinal seams are used, the finger-accepting apertures and other optional grip-enhancing features can be formed in the rectangular cardboard blanks, or they can be post-formed as discussed above. Again, the apertures may be obtained by die cutting, laser cutting, water jet cutting, thermoforming, grinding, and the like.

The apertures may be formed in the surface of the tubular element by grinding away only the outer surface of the tubular element, by laminating one or more layers with a portion of the layer removed in the shape of the aperture to one or more layers without a portion corresponding to the aperture removed, by slitting the leading and trailing edges of the aperture through the tubular element and depressing the tubular element material radially inward, and by deeply embossing a sharp edged aperture into the tubular material. Other useful aperture-forming methods will generally be known to those of ordinary skill in the art. Apertures which exist in the surface of the tubular material may therefore be opaque, or with an appropriate choice of material, they may be transparent. The bottom of the surface apertures may be treated with a contrasting color to help the user to locate these finger-accepting apertures.

The finger-accepting apertures which are formed through the tubular element at the gripper end of the applicator tube also allow for the use of contrasting color at the leading end of the inner plunger to signal the location of the apertures. This color can also be useful in compact tampon applicators which require the plunger to be partially withdrawn prior to expelling a tampon. Generic compact tampon applicators are known to those of ordinary skill in the art. The plunger can have a signalling color at its leading end to signal to the user when the plunger is sufficiently withdrawn to allow the leading end of the plunger to bear against the rear of a tampon held within the applicator.

While the detailed description above relates specifically to a tampon applicator, one of ordinary skill in the art will readily recognize that the same device can be used for the vaginal or rectal delivery of prophylactic compositions, such as spermicides, and/or medicaments, such as fungicides. These compositions and/or medicaments may be in the form of solids, creams, foams, gels, and the like.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. An insertion device for rectal or vaginal delivery of an article comprising a tubular element capable of substantially containing an insertable element, the tubular element having an outer surface, an insertion end and a gripper end, the gripper end having a plurality of means for enhancing a user's grip, each of said means comprising a finger accepting aperture in the outer surface, the apertures having leading and trailing edges corresponding to the insertion and gripper ends of the tubular element, respectively, the apertures being dimensioned to accept a portion of a user's finger and at least the leading and trailing edges of the apertures providing relatively abrupt, finger-accepting edges to frictionally resist movement of a user's finger in response to longitudinal forces on the insertion device.

2. The insertion device of claim 1 wherein the tubular element has a high-gloss outer surface.

3. The insertion device of claim 2 wherein the high-gloss outer surface is a polymeric surface.

4. The insertion device of claim 3 wherein the polymeric surface is formed from a polymer selected from the group consisting of polyethylene, polypropylene, polyester, polycaprolactone, polyvinyl alcohol, ethylene-vinyl acetate copolymer, and cellophane.

5. The insertion device of claim 2 wherein the high-gloss outer surface is a surface layer of silicone.

6. The insertion device of claim 1 wherein the tubular element comprises a cellulosic material.

7. The insertion device of claim 6 wherein the cellulosic material is paperboard or cardboard.

8. The insertion device of claim 1 wherein the tubular element is plastic.

9. The insertion device of claim 1 wherein the tubular element has a circumference and the plurality of finger-accepting apertures are approximately oppositely disposed about the circumference.

10. The insertion device of claim 1 wherein the plurality of finger-accepting apertures are substantially arranged in at least one circumferential arrangement.

11. The insertion device of claim 1 wherein the plurality of finger-accepting apertures are arranged and configured to allow skin of a user's finger to project into the aperture.

12. The insertion device of claim 1 wherein the tubular element has a circumference and the plurality of finger-accepting apertures have a major axis substantially aligned with the circumference.

13. The insertion device of claim 1 wherein the gripper end has at least one indented surface proximate the plurality of finger-accepting apertures.

14. The insertion device of claim 1 wherein the gripper end has at least one raised projection proximate the plurality of finger-accepting apertures.

15. The insertion device of claim 1 wherein the apertures completely penetrate the tubular element.

16. A tampon applicator comprising:
 a) an outer tubular element having an outer surface, an insertion end, and a gripper end, the gripper end having a plurality of finger-accepting apertures, the apertures having leading and trailing edges corresponding to the insertion and gripper ends of the tubular element, respectively, the apertures being dimensioned to accept a portion of a user's finger and at least the leading and trailing edges of the apertures providing relatively abrupt, finger-accepting edges to frictionally resist movement of a user's finger in response to longitudinal forces on the insertion device; and
 b) an inner tubular element telescopically inserted into the outer tubular element and having a leading end and a trailing end corresponding to the insertion end and gripper end, respectively, of the outer tubular element, the inner tubular element having at least one protrusion proximate the leading end which is engageable with a portion of the outer tubular element to substantially prevent the withdrawal of the inner tubular element from the outer tubular element.

17. The tampon applicator of claim 16 wherein the outer tubular element has a high-gloss outer surface.

18. The tampon applicator of claim 17 wherein the high-gloss outer surface is a polymeric surface.

19. The tampon applicator of claim 18 wherein the polymeric surface is formed from a polymer selected from the group consisting of polyethylene, polypropylene, polyester, polycaprolactone, polyvinyl alcohol, ethylene-vinyl acetate copolymer, and cellophane.

20. The tampon applicator of claim 17 wherein the high-gloss outer surface is a surface layer of silicone.

21. The tampon applicator of claim 16 wherein the outer tubular element comprises a cellulosic material.

22. The tampon applicator of claim 21 wherein the cellulosic material is paperboard or cardboard.

23. The tampon applicator of claim 16 wherein the outer tubular element is plastic.

24. The tampon applicator of claim 16 wherein the tubular element has a circumference and the plurality of finger-accepting apertures are approximately oppositely disposed about the circumference.

25. The tampon applicator of claim 16 wherein the plurality of finger-accepting apertures are substantially arranged in at least one circumferential arrangement.

26. The tampon applicator of claim 16 wherein the plurality of finger-accepting apertures are arranged and configured to allow skin of a user's fingers to project into the apertures.

27. The tampon applicator of claim 16 wherein at least a portion of the inner tubular element adjacent the leading end has a first color and the outer tubular element has a second color different than the first color whereby the apertures are readily distinguishable from other areas of the gripper end.

28. The tampon applicator of claim 16 wherein the at least one protrusion of the inner tubular element is engageable with at least one of the finger-accepting apertures of the outer tubular element to substantially prevent the withdrawal of the inner tubular element from the outer tubular element.

29. The tampon applicator of claim 16 wherein the gripper end has at least one indented surface proximate the plurality of finger-accepting apertures.

30. The tampon applicator of claim 16 wherein the gripper end has at least one raised projection proximate the plurality of finger-accepting apertures.

31. The tampon applicator of claim 16 wherein the apertures completely penetrate the tubular element.

32. A method of forming an insertion device for vaginal or rectal delivery of an article comprising the steps of forming a tubular element capable of substantially containing an insertable element, the tubular element having an insertion end and a gripper end; forming a plurality of means for enhancing a user's grip, each of said means comprising a finger accepting aperture in the griper end; wherein the finger accepting apertures are dimensioned to accept a portion of a user's finger.

33. The method of claim 32 wherein the step of forming the plurality of apertures is performed prior to the step of forming the tubular element from a tube-forming material.

34. The method of claim 32 wherein the step of forming the plurality of apertures is performed after the step of forming the tubular element.

35. The method of claim 32 further comprising the step of forming at least one raised projection in the tubular element proximate the plurality of finger-accepting apertures.

36. The method of claim 32 further comprising the step of forming at least one indented surface in the tubular element proximate the plurality of finger-accepting apertures.

37. The method of claim 32 further comprising the step of punching a tube-forming blank and the plurality of apertures from a sheet of tube-forming material.

38. The insertion device of claim 1 wherein the insertion end comprises a plurality of inwardly curved petals forming a substantially closed dome.

39. The method of claim 32 which further comprises the step of inwardly curving petals at the insertion end to form a substantially closed dome.

* * * * *